United States Patent [19]

Falk

[11] Patent Number: 4,577,036

[45] Date of Patent: Mar. 18, 1986

[54] PERFLUOROALKYL-ALKYL-THIO, SULFINYL OR SULFONYL-ALKYLENE GLYCIDYL ETHER

[75] Inventor: Robert A. Falk, New City, N.Y.

[73] Assignee: Ciba-Geigy Corporation, Ardsley, N.Y.

[21] Appl. No.: 696,552

[22] Filed: Jan. 30, 1985

[51] Int. Cl.$^4$ ................. C07D 303/46; C07D 303/36; C07D 303/34
[52] U.S. Cl. ..................................... 549/556; 549/551; 549/553
[58] Field of Search ................. 549/551, 553, 556

[56] References Cited

U.S. PATENT DOCUMENTS

| | | | |
|---|---|---|---|
| 4,104,283 | 8/1978 | Hickner | 549/556 |
| 4,113,748 | 9/1978 | Hager et al. | 549/556 |
| 4,435,330 | 3/1984 | Falk | 546/102 |

OTHER PUBLICATIONS

W. Bernheim et al., Textilveredlung, vol. 2(7), (1967), pp. 463–470.

Primary Examiner—Norma S. Milestone
Attorney, Agent, or Firm—Michael W. Glynn

[57] ABSTRACT

Perfluoroalkyl-alkyl-thio, sulfinyl or sulfonyl-alkylene glycidyl ethers of the formula

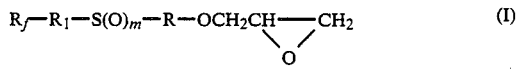

wherein
$R_f$ is perfluoroalkyl or perfluoralkoxyperfluoroalkyl of 3 to 18 carbon atoms;
$R_1$ is alkylene, carboxamidoalkylene or sulfonamidoalkylene of up to six carbon atoms and wherein the amido nitrogen is unsubstituted or substituted by lower alkyl;
m is 0, 1 or 2; and
R is alkylene of 2 to 12 carbon atoms, are useful as intermediates in preparing surfactants.

10 Claims, No Drawings

PERFLUOROALKYL-ALKYL-THIO, SULFINYL OR SULFONYL-ALKYLENE GLYCIDYL ETHER

The instant invention is directed to novel perfluoroalkyl-alkylthio (sulfinyl or sulfonyl) alkylene glycidyl ethers of the formula $$R_f-R_1-S(O)_m-R-OCH_2CH\underset{O}{\overset{}{\diagdown\diagup}}CH_2 \qquad (I)$$

wherein $R_f$ is straight or branched chain perfluoroalkyl of 3 to 18 carbon atoms or perfluoroalkoxyperfluoroalkyl of 3 to 18 carbon atoms;

$R_1$ is straight or branched chain alkylene of up to six carbon atoms, carboxamidoalkylene of up to six carbon atoms, or sulfonamidoalkylene of up to six carbon atoms, and wherein the amido nitrogen thereof is unsubstituted or substituted by lower alkyl;

m is 0, 1 or 2; and

R is straight or branched chain alkylene of 2 to 12 carbon atoms.

Preferably $R_f$ is perfluoroalkyl, more preferably straight chain perfluoroaklyl of 6 to 12 carbon atoms. Mixtures of perfluoroalkyl groups are often advantageous.

$R_1$ is preferably straight chain alkylene of 2 to 4 carbon atoms and most preferably ethylene.

The group m is preferably 0 or 2.

R is preferably straight or branched chain alkylene of 3 carbon atoms.

The compounds of formula I may be prepared by methods generally known to the art.

For example, the compounds of formula I where m is 0 may be prepared by reacting a mercaptan of the formula II $$R_f-R_1-SH \qquad (II)$$

where $R_f$ and $R_1$ are as defined above, with alkenyl glycidyl ethers of the formula $$R'-OCH_2CH\underset{O}{\overset{}{\diagdown\diagup}}CH_2 \qquad (III)$$

where R' is alkenyl of 3 to 12 carbon atoms corresponding to the alkylene group R in formula (I). This reaction is conveniently carried out in the presence of a free-radical catalyst, such as an azo type free-radical catalyst.

The reaction temperature and choice of azo-type free-radical catalyst are considered to be mutually dependent. The temperature range of 40° C. to 100° C. is one wherein the formation of undesirable by-products is minimized and wherein the reaction products are stable. In order to achieve a reasonable reaction rate of these temperatures, it is desirable to use an azo-type catalyst that is reactive to a reasonable extent in this temperature range. It is, therefore, preferred to use an azo-type free-radical catalyst having a 1-hour half-life temperature of 40° to as high as 100° C.

Suitable solvents are such in which the reactants are soluble at reaction temperatures and include aliphatic or aromatic hydrocarbons such as heptane, benzene, toluene, etc; chlorinated or fluorinated aliphatic or aromatic hydrocarbons such as methylene chloride, chloroform, methyl chloroform, carbon tetrachloride, trichloroethylene, perchloroethylene. Freons such as 1,1,2-trifluoro-1,2,2-trichloroethane, etc., chlorobenzene, benzotrifluoride or hexafluoroxylene, ketones, ester and ethers such as acetone, methyl isobutyl ketone, ethyl acetate and higher homologs, dialkyl ethers, tetrahydrofuran, ethylene glycol monomethyl or monoethyl ether, ethylene glycol dimethyl or diethyl ether, and acetonitrile.

Where convenient, it is preferred to carry out the addition reaction in bulk, i.e. in the absence of a solvent.

While the choice of conventional azo-type free-radical catalyst is not critical, 2,2'-azobis (2,4-dimethylvaleronitrile) has been found convenient.

An alternate method of preparing the compounds of formula I involves the addition of an alcohol of the formula $$R_f-R_1-S(O)_m-R-OH \qquad (IV)$$

where $R_f$, $R_1$, m and R are as defined above, with an epihalohydrin of the formula V $$X-CH_2-CH\underset{O}{\overset{}{\diagdown\diagup}}CH_2 \qquad (V)$$

where X is halo, preferably chloro, to form the corresponding halohydrin VI $$R_f-R_1-S(O)_m-R-OCH_2CH-CH_2X \qquad (VI)$$
$$\underset{OH}{|}$$

where $R_f$, $R_1$, m, R and X are defined above, followed by dehydrohalogenation to remove the hydrogen halide, HX, and form the corresponding glycidyl ether of formula I.

In this alternative method of preparing the compounds of formula I, the alcohol of formula IV is reacted with the halohydrin, such as epichlorohydrin, in bulk or in a common dry and aprotic solvent, including ketones, such as acetone or methyl ethyl ketone; ethers, such as diethylether, ethyleneglycol-dimethylether or tetrahydrofuran; esters such as ethyl acetate or methyl cellosolve acetate; aromatic hydrocarbons, such as toluene, and amides, such as dimethylformamide or N-methyl pyrrolidone. A Lewis acid catalyst, such as boron trifluoride (usually in the form of the diethyl ether complex thereof) or aluminum chloride, is used to promote the formation of the halohydrin intermediate. If the reaction is run in the absence of a solvent, it is advantageously run at a temperature above the melting point of the compound with boron trifluoride-etherate. The reaction is ordinarily exothermic. It is generally not necessary to isolate the halohydrin intermediate, and the dehydrohalogenation can be carried out in the same reaction vessel to form the glycidyl ether of formula I.

The dehydrohalogenation of the halohydrin of formula VI to form the glycidyl ether of formula I is advantageously achieved by contacting the halohydrin of formula VI with a base, preferably using a stoichiometric amount, or slight excess of base.

Suitable bases include sodium hydroxide, potassium hydroxide, pyridine, lutidine and triethylamine. Conveniently, a solvent is selected which dissolves the reactants and desired product, but not the by-product salt, so that the salt will precipitate out as the reaction proceeds and can then be removed by conventional techniques, such as filtration.

The dehydrohalogenation reaction is conveniently conducted between about 20° C. and 100° C. in aqueous/organic media, such as an aqueous/lower alkanol media or aqueous/organic hydrocarbon media such a aqueous/toluene media. When the reaction is conducted in a two phase medium a phase transfer catalyst such as di-dodecyl dimethyl ammonium hydroxide or tetrabutylammonium hydrogen sulfate can be employed to accelerate the reaction.

Typically, a stoichiometric amount of a base, such as 50% aqueous sodium hydroxide, is slowly added to the reaction mixture. The resulting reaction is exothermic and the reaction temperature is advantageously maintained between about 20°-60° C. with stirring for 1-3 hours. The resulting epoxide has the formula (I).

The by-product salt is removed from the epoxide intermediate and any residual solvent is removed by vacuum distillation. The product may be used without further purification or distilled if necessary.

The instant perfluoroalkyl group containing epoxides are very reactive and can be used prepare highly surface-active fluorosurfactants.

Thus, the compounds of formula I can be reacted with amine sulfur trioxide complexes, such as trimethylamine sulfur trioxide, N-methylpyrrolidonesulfur trioxide, and the like, to form useful surfactants having low surface and interfacial tension properties. The reaction can be performed in accordance with the general and specific disclosures set forth in U.S. Pat. No. 4,435,330, incorporated herein by reference. The resulting sulfato betaine surfactants find utility as cleaning agents, as leveling agents for floor waxes and as aqueous wetting agents in firefighting compositions.

Suitable amine sulfur trioxide complexes for use in reaction with the compounds of formula I are complexes of the formula VII

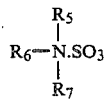

(VII)

wherein $R_5$, $R_6$ and $R_7$ are independently lower alkyl, and $R_6$ may also represent benzyl, and $R_6$ and $R_7$ taken together with the nitrogen to which they are attached may also represent piperidino or morpholino, or $R_5$, $R_6$ and $R_7$ taken together with the nitrogen to which they are attached, may represent pyridyl, acridyl or quinolyl. The reaction between the glycidyl ethers of formula I and the amine sulfur trioxide complexes of formula VII advantageously takes place by reacting stoichiometric amounts of each at a temperature between 30° and 180° C., optionally in the presence of a solvent, such as N-methylpyrrolidone.

Alternately, the compounds of formula I can be reacted with an amino acid of the formula

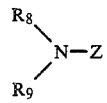

(VIII)

wherein $R_8$ and $R_9$ are hydrogen, or lower alkyl; and Z is alkylene of up to 12 carbon atoms which is substituted by carboxy, sulfo, phosphoro or phosphono. Suitable compounds of formula VIII include glycine, alanine, aspartic acid, sarcosine, 2-aminoethyl hydrogen phosphate, taurine and methyl taurine.

The addition of glycidyl epoxide of formula I to amino acid of formula VIII is a base catalyzed 1:1 reaction which occurs most readily in a single phase. This is generally provided in an aqueous solvent mixture by choice of a suitable water miscible cosolvent such as methanol, isopropanol, butoxyethanol and the like. The reaction is generally conducted at temperature from 25° to 200°, but preferably from 50° to 130°.

The reaction can be run uncatalyzed if the reactant is sufficiently basic or at an alkaline pH provided by alkali hydroxide, ion-exchange catalyst or a non-reactive base, e.g. triisopropylamine.

The products are generally useful without isolation but can be isolated depending on the pH, in acid foam, as isoelectronic neutral salts or as alkali metal or ammonium salts. The fully quaternized derivatives containing N-lower alkyl or N-benzyl quaternary functions are generally isolated as neutral zwitterionic compounds or acid adducts, e.g. hydrochlorides.

The resulting amphoteric compounds are very stable to hydrolysis and find numerous uses as surfactants and wetting agents. Since they are derived from readily available amino acids and certain readily available fluorinated epoxides they comprise particularly useful compositions.

The alcohols of formula IV are known or can easily be prepared from known compounds by methods known per se. Thus, for example, the alcohols of formula IV can easily be prepared by reacting a mercaptan of formula (II), as described above, with either a haloalkanol of the formula IX $$X-R-OH \qquad \text{(IX)}$$

where X and R are as defined above, or an unsaturated alcohol of the formula X $$R'-OH \qquad \text{(X)}$$

wherein R' is defined above.

The reaction between II and IX can easily be performed by reacting stochiometric amounts of each in the presence of a base to remove the acid halide (HX) formed, in the presence or absence of an inert solvent, at a reaction temperature between 30° C. and 120° C., and removing the by-product salt, e.g. by washing with water. Suitable bases include alkali metal hydroxides and carbonates, alkaline earth metal hydroxides and carbamates and amines such as trimethylamine or pyridine. Sufficient base should be added during the course of the reaction to react with all hydrogen halide formed. Where employed, suitable inert solvents include tetrahydrofuran, dimethylsulfoxide, lower alkanols and the like.

In reacting the mercaptan of formula II with an unsaturated alcohol of formula X to obtain the corresponding alcohol of formula IV, the simple addition reaction is conveniently conducted in the presence of a free radical initiator, such as an azo-type free-radical initiator, for example 2,2'-azobis (2,4-dimethylvaleronitrile), in the presence or absence of an inert solvent such as tetrahydrofuran, methyl ethyl ketone, dimethylsulfoxide or the like, at a reaction temperature between about 30° and 100° C.

In order to obtain those compounds of formula IV wherein m equals 1 or 2 from the corresponding thioether alcohol, where m equals 0, the thioether alcohol of formula IV is oxidized with an oxidizing agent. Suitable oxidizing agents include hydrogen peroxide in an organic acid medium, such as acetic acid. The reaction is conducted at a temperature of between about 30° C. to 100° C. until the thioether alcohol is converted to the corresponding sulfoxide or sulfone. In general, lower temperatures e.g. between about 30° C. and 50° C. favor the formation of the sulfoxide, where m=1, whereas more elevated temperatures, e.g. between about 50° C. and 100° C., favor the formation of the corresponding sulfones. Moreover, the formation of sulfoxide can be enhanced by reducing the amount of peroxide employed to a 1:1 mole ratio, whereas a substantial excess of peroxide generally favors the formation of sulfones.

Similarly, the compounds of formula I wherein m equals 0 can be converted into the corresponding sulfoxides and sulfones, i.e. where m is 1 or 2, by oxidation with a suitable oxidizing system which does not affect the glycidyl moiety, such as a perbenzoic acid, e.g. meta-chloroperbenzoic acid, in the presence of an inert solvent, such as a halogenated hydrocarbon, e.g. chloroform, or the like, at a reaction temperature between about 10° C. to about 50° C. Again elevated temperatures and an excess of peroxide favor the formation of sulfone.

The present invention is more clearly understood with reference to the following non-limiting Examples. All parts are by weight unless otherwise specified.

EXAMPLE 1

A mixture of 1-allyloxy-2,3-epoxy propane (24.1 g, 0.212 mol) and 2,2'-azobis (2,4-dimethylvaleronitrile) (0.99 g, 0.004 mol) was added dropwise between 60°–75° within 40 minutes under nitrogen to a solution of 1,1,2,2,-tetrahydroperfluoro-octane)thiol (77.26 g, 0.202 mol) in 11 g toluene. The reaction mixture was stirred for 3 hours at 65°–70° C. and the toluene distilled off at 80° C. under aspirator vacuum (25 mm) to yield 99.2 g (99% of theory) of a clear colorless liquid in a 10:1 ratio of the isomers I and II.*

$$C_6F_{13}CH_2CH_2SCH_2CH_2CH_2OCH_2CH\underset{O}{\overset{}{-\!\!\!-\!\!\!-}}CH_2 \quad I*$$

$$C_6F_{13}CH_2CH_2S\underset{CH_3}{\overset{|}{C}H}CH_2OCH_2CH\underset{O}{\overset{}{-\!\!\!-\!\!\!-}}CH_2 \quad II$$

Titration with perchloric acid in the presence of tetrabutylammonium iodide resulted an equivalent mol weight of 509 (theory 494). NMR showed proton resonances at δ 1.85, 2 protons (—SCH$_2$CH$_2$CH$_2$O); δ 2.37, 2 protons (C$_6$F$_{13}$Ch$_2$CH$_2$); δ 2.69, 6 protons

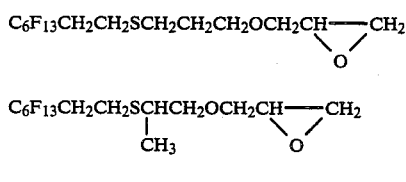

δ 3.11, 1 proton

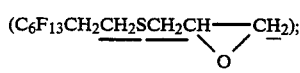

δ 3.33 and δ 3.71,2 protons (O—CH$_2$); and δ 3.57 (CH$_2$OCH$_2$).

Analysis for C$_{14}$H$_{15}$F$_{13}$O$_2$S: Calc: C, 34.0; H, 3.0; Found: C, 33.9; H, 3.0.

EXAMPLE 2

1,1,2,2,-tetrahydroperfluoroalkylthiol (distribution represents a mixture of 2.1% C$_4$, 37.6% C$_6$, 34.3% C$_8$, 19.0% C$_{10}$, 5.5% C$_{12}$, 1.0% C$_{14}$) (279.6 g; 0.615 mol) and a solution of 1-allyloxy-2,3-epoxypropane (73.6 g; 0.646 mol) and 2,2' azobis (2,4 dimethylvaleronitrile) 3.05 g; 0.012 mol) are added parallel under nitrogen at 60° within 90 minutes through two separate addition funnels into a reaction flask. The reaction mixture was stirred for another hour at 60° to yield 342.7 g (98% of theory) as a slight yellow gel. GC Analysis showed 99% assay in a 10:1 ratio of the isomers I and II.*

$$R_fCH_2CH_2SCH_2CH_2CH_2OCH_2CH\underset{O}{\overset{}{-\!\!\!-\!\!\!-}}CH_2 \quad I*$$

$$R_fCH_2CH_2S\underset{CH_3}{\overset{|}{C}H}CH_2OCH_2CH\underset{O}{\overset{}{-\!\!\!-\!\!\!-}}CH_2 \quad II$$

Titration with perchloric acid in the presence of tetrabutylammoniumiodide resulted in an equivalent mol weight of 573 (theory 569). NMR showed the same proton resonances as in example 1.

EXAMPLE 3

1,1,2,2,-tetrahydroperfluoroalkylthiol (distribution represents a mixture of 0.2% C$_4$, 0.4% C$_6$, 8.4% C$_8$, 28.0% C$_{10}$, 39.1% C$_{12}$, 18.1% C$_{14}$, 4.3% C$_{16}$) (90.0 g, 0.138 mol) was metered parallel with a solution of 2,2'-azobis-(2,4-dimethylvaleronitrile) (0.8 g, 0.003 mol) and 1-allyloxy-2,3-epoxy propane (16.5 g, 0.145 mol) in two separate feeds between 65°–70° under nitrogen into a reaction flask, charged with 24 g toluene. The reaction was stirred at 85° for 90 minutes and the toluene evaporated at room temperature under high-vacuum to yield 100.4 g (95% of theory) as a white crystalline solid with a melting point of 78°–107°. GC Analysis showed at 99% assay in a 10:1 ratio of the isomers I and II.*

$$R_fCH_2CH_2SCH_2CH_2CH_2OCH_2CH\underset{O}{\overset{}{-\!\!\!-\!\!\!-}}CH_2 \quad I*$$

$$R_fCH_2CH_2S\underset{CH_3}{\overset{|}{C}H}CH_2OCH_2CH\underset{O}{\overset{}{-\!\!\!-\!\!\!-}}CH_2 \quad II$$

Titration with perchloric acid in the presence of tetrabutylammoniumiodide resulted in an equivalent mol weight of 756 (theory 767).

EXAMPLE 4

A solution of m-chloroperbenzoic acid (64.8 g 80%, 0.3 mol) in 800 ml chloroform was added dropwise under nitrogen within 5 hours to a isomeric mixture of 1-[(1,1,2,2,-tetrahydroperfluoro-octylthio)-1-propyloxy]-2,3-epoxy propane and 1-[(1,1,2,2,-tetrahydroperfluoro-octylthio)-2-propyloxy]-2,3-epoxy propane (74.1 g, 0.15 mol) dissolved in 400 ml chloroform. The slight exothermic reaction was kept between 25°–35° during the addition and stirred at room temperature overnight. The precipitated m-chlorobenzoic acid was filtered off and the filtrate washed twice with ice cold 10% NaOH, once with ice cold brine and once with ice-water. The organic layer was dried over MgSO$_4$, evaporated to dryness and dried under high vacuum overnight to yield 73.5 g (93% of theory) as a white crystalline solid with a melting point of 61°–64° (103° clear). GC Analysis showed a 94% assay in a 10:1 ratio of the isomers I and II.*

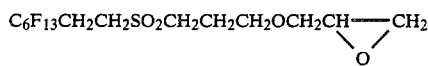 I*

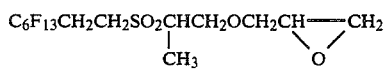 II

Titration with perchloric acid in the presence of tetrabutylammoniumiodide resulted in an equivalent mol weight of 534 (theory 526). NMR showed proton resonances at δ 2.13, 2 protons (SO$_2$CH$_2$C$\underline{H}_2$CH$_2$O—); δ 2.57, 1 proton

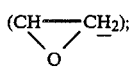

δ 2.67, 2 protons (C$_6$F$_{13}$C$\underline{H}_2$); δ 2.77, 1 proton

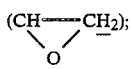

δ 3.11, 1 proton

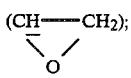

δ 3.23 4 protons (C$_6$F$_{13}$CH$_2$C$\underline{H}_2$SO$_2$C$\underline{H}_2$);
δ 3.31, 1 proton (O—C$\underline{H}_2$CH); δ 3.63 2 protons (SO$_2$CH$_2$CH$_2$C$\underline{H}_2$) and δ 3.79, 1 proton (O—CH$_2$C$\underline{H}$).
Analysis for C$_{14}$H$_{15}$F$_{13}$O$_4$S: Calc: C, 31.9; $\overline{H}$, 2.85; Found: C, 33.1; H, 2.9.

EXAMPLE 5

A 10:1 isomeric mixture of 1-[(1,1,2,2,-tetrahydroperfluorooctylthio)-1-propyloxy]-2,3-epoxy propane and 1-[(1,1,2,2,-tetrahydroperfluorooctylthio-)-2-propyloxy]-2,3-epoxy propane (14.8 g, 0.03 mol) in 42.2 g 2-propanol and 10 g deionized water was reacted at 60° for 5 hours with N-methyltaurine-sodium salt (11.4 g 42.2% in H$_2$O; 0.03 mol) under nitrogen. The clear yellow solution was dialized for 24 hours and the water removed in a draft-oven at 80° C., the yellow residual gum dissolved in hot acetone, evaporated and dried under high vacuum overnight to yield an amorphous residue.

Analysis for C$_{17}$H$_{23}$F$_{13}$NO$_5$S$_2$Na: Calc: C, 31.8; H, 3.58; N, 2.18; F, 38.5; Found: C, 31.6; H, 3.5; N, 2.0; F, 38.5.

Isomeric mixture of:

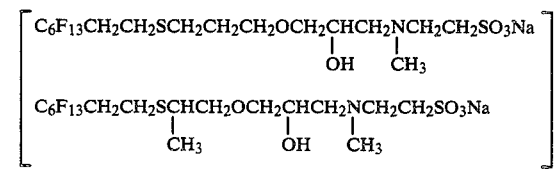

EXAMPLE 6

A comparison of the surfactant properties of Example 5 to the corresponding properties of a surfactant prepared from

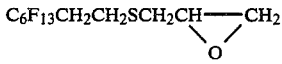

show the advantages of the subject glycidyl ether.

| | Comparative Surfactant Properties | | | | | | | | | |
|---|---|---|---|---|---|---|---|---|---|---|
| | Ross-Miles at 0.1%[1] | | | Draves Wetting in sec.[2] | Equilibrium Surface Tension[3] (dynes/cm) | | | Interfacial Surface Tension[4] (dynes/cm) | | |
| Structure | De-ionized | 300 ppm | Sea | | 0.1% | 0.01% | 0.001% | 0.1% | 0.01% | 0.001% |
| C$_6$F$_{13}$CH$_2$CH$_2$S(CH$_2$)$_3$OCH$_2$CHCH$_2$N(CH$_2$)$_2$SO$_3$⁻ \| OH \| CH$_3$ | 178/155 | 163/153 | 78/64 | 21.8 | 18.5 | 18.0 | 29.3 | 6.0 | 7.8 | 16.4 |
| C$_6$F$_{13}$CH$_2$CH$_2$SCH$_2$CHCH$_2$N(CH$_2$)$_2$SO$_3$⁻ \| OH \| CH$_3$ | 190/174 | 85/80 | incomp. | 50.0 | 21.7 | 26.8 | 40.5 | 11.0 | 19.1 | 32.3 |

[1]ASTM-Method D-1173-53, at room temperature, initial foam height in mm and after 5 minutes.
[2]ASTM-Method D-2281-68, sinking time in sec
[3]ASTM-Method D-1331-56, DuNouy tensiometer
[4]ASTM-Method D-1331-56, DuNouy tensiometer

EXAMPLES 7–10

Using the methods described and by techniques analogous to Examples 1–6, the following glycidyl ethers and derived surfactants are prepared:

| Example | Glycidyl Ethers | Rf-Surfactant |
|---|---|---|
| 7 | 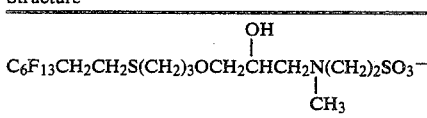 C$_8$F$_{17}$SO$_2$N(CH$_3$)CH$_2$CH$_2$S(CH$_2$)$_3$OCH$_2$CH—CH$_2$ \ O / | C$_8$F$_{17}$SO$_2$N(CH$_3$)CH$_2$CH$_2$S(CH$_2$)$_3$OCH$_2$CHCH$_2$NCH$_2$CH$_2$SO$_3$Na \| \| OH CH$_3$ |

-continued

| Example | Glycidyl Ethers | Rf-Surfactant |
| --- | --- | --- |
| 8 | $C_7F_{15}CONHCH_2CH_2S(CH_2)_3OCH_2CH\underset{O}{-\!\!-\!\!-}CH_2$ | $C_7F_{15}CONHCH_2CH_2S(CH_2)_3OCH_2\underset{\underset{OH}{\mid}}{C}HCH_2\underset{\underset{CH_3}{\mid}}{N}CH_2CO_2Na$ |
| 9 | $C_6F_{13}CH_2CH_2S(CH_2)_{11}OCH_2CH\underset{O}{-\!\!-\!\!-}CH_2$ | $C_6F_{13}CH_2CH_2S(CH_2)_{11}OCH_2\underset{\underset{OSO_3^-}{\mid}}{C}HCH_2\overset{+}{N}(CH_3)_3$ |
| 10 | $(CF_3)_2CFO(CF_2)_3CH_2CH_2SO_2(CH_2)_3OCH_2CH\underset{O}{-\!\!-\!\!-}CH_2$ | $(CF_3)_2CFO(CF_2)_3CH_2CH_2SO_2(CH_2)_3OCH_2\underset{\underset{OSO_3^-}{\mid}}{C}H-CH_2\overset{+}{N}(CH_3)_3$ |

I claim:

1. A perfluoroalkyl-alkylthio(sulfinyl or sulfonyl)-alkylene glycidyl ether of the formula $$R_f-R_1-S(O)_m-R-OCH_2CH\underset{O}{-\!\!-\!\!-}CH_2 \qquad (I)$$

wherein $R_f$ is straight or branched chain perfluoroalkyl of 3 to 18 carbon atoms or perfluoroalkoxyperfluoroalkyl of 3 to 18 carbon atoms;

$R_1$ is straight or branched chain alkylene of up to six carbon atoms, carboxamidoalkylene of up to six carbon atoms, or sulfonamidoalkylene of up to six carbon atoms, and wherein the amido nitrogen thereof is unsubstituted or substituted by lower alkyl;

m is 0, 1 or 2; and

R is straight or branched chain alkylene of 2 to 12 carbon atoms.

2. A compound according to claim 1 wherein $R_f$ is perfluoroalkyl.

3. A compound according to claim 2 wherein $R_f$ is straight chain perfluoroalkyl of 6 to 12 carbon atoms or a mixture thereof.

4. A compound according to claim 1, wherein $R_1$ is straight chain alkylene of 2 to 4 carbon atoms.

5. A compound according to claim 4, wherein $R_1$ is ethylene.

6. A compound according to claim 2, wherein $R_1$ is straight or branched chain alkylene of up to 6 carbon atoms.

7. A compound according to claim 1, wherein m is 0 or 2.

8. A compound according to claim 1, wherein m is 0.

9. A compound according to claim 1, wherein R is straight or branched chain alkylene of 3 carbon atoms.

10. A compound according to claim 9 wherein $R_1$ is ethylene and m is 0.

* * * * *